United States Patent
Mumm et al.

(12) 
(10) Patent No.: US 6,398,731 B1
(45) Date of Patent: Jun. 4, 2002

(54) METHOD FOR RECORDING ULTRASOUND IMAGES OF MOVING OBJECTS

(75) Inventors: Bernard M. Mumm, Mammendorf; Johannes Waldinger, Neubiberg; Dietmar Kaiser, Moosburg, all of (DE)

(73) Assignee: Tomtec Imaging Systems GmbH, Unterschleibheim (DE)

( * ) Notice: Subject to any disclaimer, the term of this patent is extended or adjusted under 35 U.S.C. 154(b) by 0 days.

(21) Appl. No.: 09/463,512

(22) PCT Filed: Jul. 16, 1998

(86) PCT No.: PCT/EP90/04430
§ 371 (c)(1),
(2), (4) Date: Jan. 25, 2000

(87) PCT Pub. No.: WO99/05542
PCT Pub. Date: Feb. 4, 1999

(30) Foreign Application Priority Data

Jul. 25, 1997 (DE) .......................... 197 32 125

(51) Int. Cl.⁷ .............................. A61B 8/00; A61B 8/13
(52) U.S. Cl. ....................................... 600/437; 600/454
(58) Field of Search ................................. 600/437, 441, 600/442, 443, 447, 453, 454, 455, 456, 466, 440; 128/916; 73/626, 628; 378/145–147

(56) References Cited

U.S. PATENT DOCUMENTS

| 4,274,422 A | 6/1981 | Anderson et al. | ........... 600/440 |
|---|---|---|---|
| 4,572,202 A | 2/1986 | Thomenius | ................. 600/443 |
| 4,991,589 A | 2/1991 | Hongo et al. | ............... 600/455 |
| 5,315,512 A | * 5/1994 | Roth | ..................... 364/413.25 |
| 5,690,111 A | 11/1997 | Tsujino | ........................ 600/440 |
| 5,876,345 A | * 3/1999 | Eaton et al. | ................. 600/466 |
| 5,924,989 A | * 7/1999 | Polz | ........................... 600/443 |
| 5,935,069 A | 8/1999 | Chandler et al | ............ 600/443 |
| 6,171,248 B1 | * 1/2001 | Hossack et al. | ............ 600/459 |
| 6,231,508 B1 | 5/2001 | Miller et al. | ................. 600/437 |

FOREIGN PATENT DOCUMENTS

| DE | 0736284 A2 | * 10/1996 | ............ A61B/8/13 |
|---|---|---|---|
| DE | 0802423 A1 | * 10/1997 | ......... G01R/33/567 |

* cited by examiner

*Primary Examiner*—Marvin M. Lateef
*Assistant Examiner*—Ali M. Imam
(74) *Attorney, Agent, or Firm*—Sheridan Ross P.C.

(57) ABSTRACT

An apparatus and method for recording ultrasound images of a moving object is disclosed. The apparatus includes an ultrasound transmitter, an ultrasound receiver, and an image processor. At least one of the ultrasound transmitter and receiver is moved in relation to an object. Images of the object are acquired, and a movement state of the object is determined and classified into one of two movement states. Based on the movement state of the object, images are either not acquired, or not processed. If the image of the object is not processed, the image processor filters out the images which were acquired during a movement state of the object when the movement is high. The image processor then assembles the images and displays the assembled images.

76 Claims, 3 Drawing Sheets

Phase I

Phase II

Phase III

Phase IV usw.

METHOD FOR RECORDING ULTRASOUND IMAGES OF MOVING OBJECTS

FIELD OF THE INVENTION

The invention relates to a method for recording ultrasound images of moving objects, more particularly of blood vessels or organs of living things or, respectively, organisms according to the preamble of claim 1.

BACKGROUND OF THE INVENTION

In order to record objects by means of ultrasound devices, an ultrasound transmitter is directed towards the object for transmission of ultrasound waves, while an ultrasound receiver receives the ultrasound waves reflected by the object. For the purpose, ultrasound heads are commonly used, which include both the ultrasound transmitter and the ultrasound receiver. In order to record a plurality of two-dimensional images, these ultrasound heads are moved along the object to be examined, while a plurality of individual images of the object are taken. The ultrasound head may be moved linearly, circularly, in an arcshape or in any other direction, for instance in a freehand manner. These images represent individual partial image areas of the object and are put together in a data processing system so that there results a three-dimensional volume image. The three-dimensional volume image consists of individual partial image areas which are "piled-up" and respectively represent individual "layers" of the object to be examined. Due to the movement of the ultrasound head along the object to be examined, the latter is scanned in layers, wherein the number of layers per length unit determines the resolution of the resulting ultrasound image in a linear scanning process. For circular or other scanning movements, the ultrasound images are put together according to the incremental image of individual partial image areas and represented.

The movement of the sound head may be realised by a mechanism, a sound diverting means integrated in the sound head or by free hand images with magnetic or optical sensor systems for the three-dimensional assignment of the ultrasound images. Assignment of the individual "layers" of the object may for instance also be implemented via the method of the parallel patent application filed by applicant. The ultrasound images are put together to sense the third dimension, commonly in a data processing system which senses the video output signal or a digital output signal of the ultrasound system and evaluates it correspondingly. The ultrasound head or, respectively, the ultrasound receiver provides the corresponding signals.

Images of objects, which generate a blurred movement due to their proper movement or the movement of adjacent objects, are usually taken in synchronization with this movement. Without the synchronization with the corresponding movement of the object (stroboscopic image), there results an unsharp image or, respectively, representation of the object in each of its movement states. In an image synchronised onto the movement of the object, one volume image is generated per movement state of the respective object. One example thereof is the three-dimensional ultrasound image of the heart. The corresponding volume images of the heart successively show all stages (phases) between the contraction (systole) and the slackening of the heart (diastole). The successive representation of individual volume images of the heart corresponds to a four-dimensional representation of the heart, the fourth dimension representing the corresponding heart movement.

For the diagnosis of the individual states of the object to be examined at specific moments of the corresponding object movement, it is just one state of the object which is important. For instance, the respective organ state is important for a purposeful diagnosis at specific moments of the electrocardiogram or the respiration, the movement of the stomach or the peristalsis of the oesophagus of a patient. For instance, the stenosis (stricture) of a blood vessel is observed at the moment of diastole.

If blood vessels or organs are recorded, a single layer is recorded per movement cycle, e.g. the systole-diastole cycle (RR interval) (see FIG. 3). The image recording velocity to be achieved is very low. For images following the heart movement, i.e. the pulse frequency of the patient, about one layer is recorded per second if the pulse frequency is about 60 heart beats per minute. The image quality to be achieved is good, but the long recording times are not acceptable in most routine cases.

During the image recording of coronary vessels by means of a catheter, the time for the examination must be kept very short since the catheter closes the vessel completely or partially, which constitutes a risk factor for the patient. Here, the long recording times mentioned above are equivalent to high stress for the patient.

Movements of the patient, which lead to movement artifacts in the three-dimensional or four-dimensional image, cannot be excluded over the long time taken for the image recording, for instance for the carotid artery (swallowing, sneezing, coughing, head or throat movement etc . . . ). Then there result artifacts like blurred portions in the ultrasound images (the spatially incorrect assignment of individual ultrasound images corresponding to the partial image areas due to the organ or part of the organ being shifted or due to the assignment between organ/ultrasound head). As one solution, conventional methods use very large strokes per layer or operate with a very quick sound head movement along the object to be examined. This leads to an inhomogeneous resolution in the three-dimensional volume image in the direction of sound head movement.

Approximately 25 layers per second are recorded in a continuous image recording and with a coupling of the sound head with the video standard, e.g. PAL. However, the three-dimensional image is strongly impaired by the movement of the organ or the blood vessel during systole and during diastole. It is only in a restricted manner that the images may be used for subsequent evaluation and the doctor may possibly misinterpret the image contents (see FIG. 2).

SUMMARY OF THE INVENTION

It is the object underlying the invention to minimize the movement blur during the recording of ultrasound images of a moving object and simultaneously to shorten the image recording time. The method is to be easy to handle and shall be realised with conventional ultrasound devices and data processing systems.

The object of the invention is met by the characterising features of claim 1. Special embodiments of the invention are characterised in the subclaims.

While the ultrasound head is moved along the object for recording individual partial image areas of the moving object and produces images of the object at certain moments, which represent the individual "layers" of the object and are later put together to form a three-dimensional volume image in the data processing system, the movement states of the object are sensed in addition to the individual partial image areas. The images of the individual partial image areas are then assigned to the movement states of the object and put together and represented in correspondence with the movement states of the object.

More particularly, the moments for recording individual partial image areas of the object are controlled by the movement sequences of the object. For instance, the moments for recording the individual partial image areas of the moving object are fixed or controlled such that no or only few images are taken during the greatest movement of the moving object and several images are taken at moments when the object moves only little.

In order to record blood vessels or organs of an organism, no or only few images are taken during the systolic cycle and several images of individual partial image areas of the blood vessel or the organ are taken during the diastolic cycle. If the movement of the object to be examined is known, the individual partial image areas may also be recorded at discrete moments, i.e. ones which are fixedly defined. In order to record objects within an organism, which are moved by the heart beat in particular, it is suitable to control the recording moments for individual partial image areas via the signals of the electrocardiogram of the organism.

While the ultrasound head is moved along the organ of the organism, individual images of different partial image areas of the organ are taken continuously. By coupling the recording times with the ECG of the organism, the systole is left out, i.e. no images are taken over a period of about 200 ms (at a pulse frequency of 60), in order to subsequently take several images about every 120 to 200 ms in correspondence with the electrocardiogram during the diastole. This is also possible via continuous recording of images of the organ, the data processing selecting the corresponding images and processing the desired images. Thus, the corresponding images are left out during the time of the greatest movement artifacts due to pulsation whereas every fifth image is taken, for instance, at a recording velocity of 25 layers per second, for instance. Therein, the scanning movement of the ultrasound head is a continuous one. One thereby achieves an approximately homogeneous local resolution for the scan of about four layers per second.

The method may employed in the IVUS region, in particular. Here, long recording times are inacceptable in the patient's interest (e.g. 30 mm with 0.1 mm increment at a pulse of 60 beats per minute: this corresponds to about 300 layers and results in an overall recording time of about 5 minutes).

With the method according to the invention, the recording time may be reduced to about 25% of conventional recording times (with ECG triggering). Advantageously, no images are analyzed during the systolic cycle and about 2 to 20, more particularly 2 to 10 images of individual partial image areas of the moving organ are evaluated. More particularly, the method is suited for flow representations, i.e. representations of the moving object or, respectively, individual regions of the object, which are marked with colours.

The method may also be realized in that the ultrasound head continuously records individual partial image areas of the object during the movement along the object to be examined and that, subsequently, a data processing system filters out the images of moments of greatest movement of the object. This filtering-out is also expedient with a recording method wherein the moments for recording individual partial image areas are controlled by the electrocardiogram of the organism, namely when extrasystoles, i.e. extraordinary movements of the organ or, respectively, the object to be examined occur during diastole, and these images may then be filtered out. By purposeful filtering, usable images of patients suffering from arrhythmia may also be taken, while it must be made sure that a sufficient number of images may be taken during the slackened heart phases.

If the partial image areas of an object are recorded continuously, it is possible to combine the ultrasound images respectively associated with the individual movement states of the object in a state image of the object. One respective phase of the object results in a corresponding volume image via the combination of a plurality of ultrasound images which had been taken at a specific movement state. The successive stringing-together of these volume images results in a representation of the movement sequence of the object in real time, comparable to a "film". A so-called four-dimensional representation of the moving object is possible despite short recording times.

BRIEF DESCRIPTION OF THE DRAWINGS

A special embodiment will be explained upon reference to the drawings as follows. Therein.

DETAILED DESCRIPTION

Figure 1:
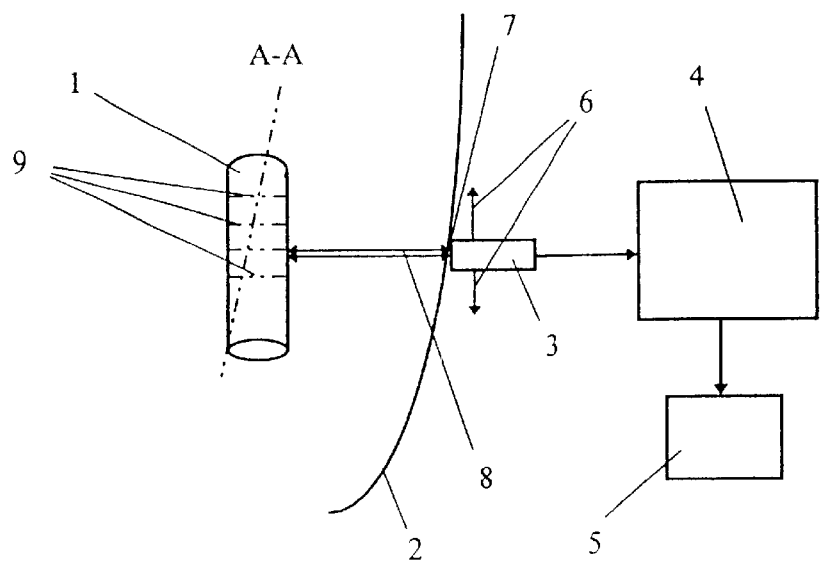
FIG. 1 is a section through an ultrasound system (ultrasound image examination arrangement) for examining the carotid artery of a patient.

FIG. 1 shows the schematic representation of the ultrasound image examination arrangement for examining the carotid artery, i.e. for examining a moving object 1. An ultrasound head 3 is moved in moving direction 6 along object 1 to be examined while different "layers", i.e. partial image areas 9 of object 1 are recorded. Between ultrasound head 3 and body wall 2, there usually is a sound medium like, for instance, oil, gel or water, which guides ultrasound waves 8 from ultrasound head 3 to body wall 2. Ultrasound head 3 provides the corresponding image signals to a data processing system 4 which transmits, after processing of the ultrasound images, a three-dimensional or four dimensional (i.e. a moving three-dimensional image) to a display device 5.

The individual partial image areas 9 are put together in data processing system 4 so that there results a three- or four-dimensional image in display device 5. Either data processing system 4 or a control device, which is not represented here, is in charge of driving ultrasound head 3 and moving ultrasound head 3.

Figure 2:
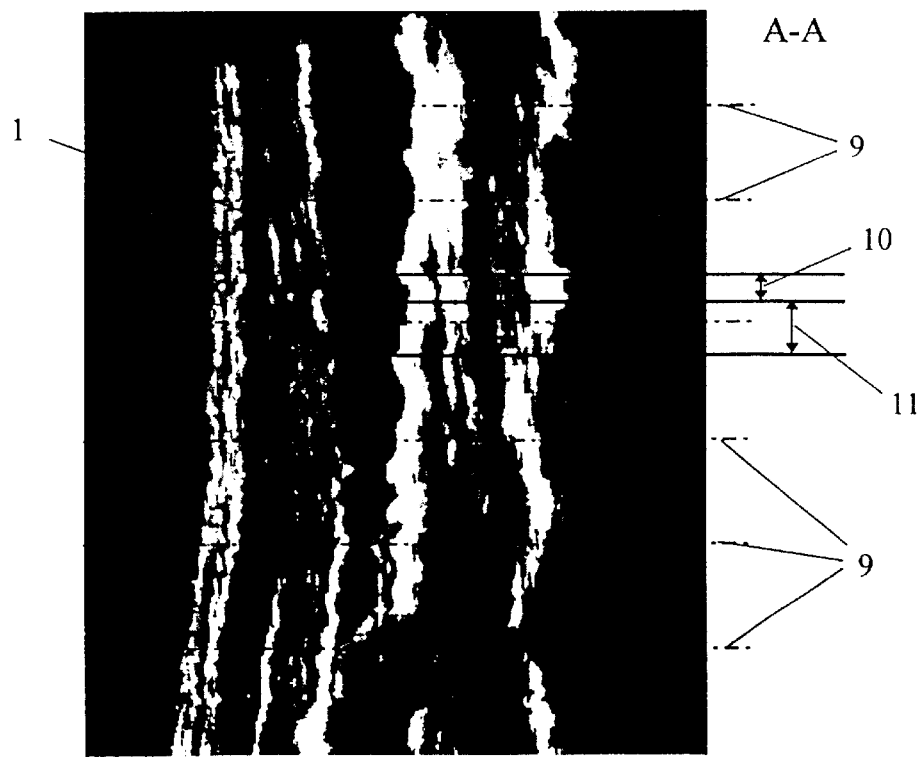
FIG. 2 shows a resulting ultrasound image for an unsynchronized, i.e. continuous recording of images of the carotid artery according to FIG. 1 via a conventional method.

FIG. 2 shows the section A—A according to FIG. 1 through the carotid artery of a patient to be examined, the ultrasound image shown here having been produced by continuous recording of individual partial image areas 9.

In the ultrasound image according to FIG. 2, one recognizes the wall of a carotid artery being represented as a wavy line which has been produced in that the carotid artery moves, due to the patient's heartbeat during the scanning process (about 25 images per second), i.e. comprises respectively larger or smaller diameters and that these varying diameters are represented in an image. Thus, there results a smaller or, respectively, a larger diameter or, respectively, a changing position of the carotid artery during the systole and the diastole of the heart. In the ultrasound image according to FIG. 2, one recognizes about 8 pulse beats of the heart, each pulse beat being subdivided into a systolic cycle 10 and a diastolic cycle 11. The individual partial image areas 9 are represented schematically, the ultrasound image shown here having been built up of about 200 partial image areas 9.

Figure 3:
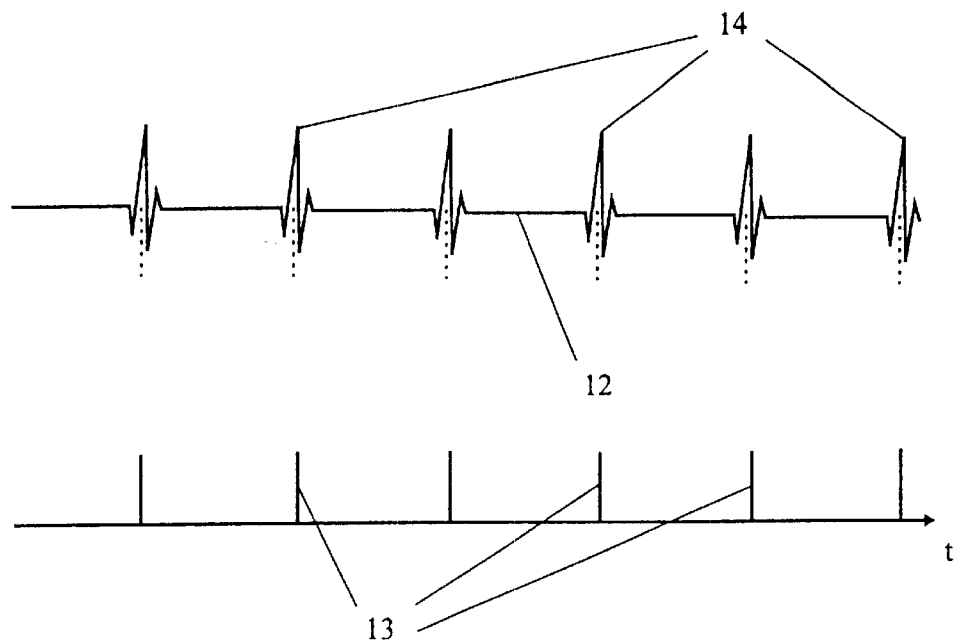
FIG. 3 shows the schematic representation of the heart beat (e.g. ECG) as well as the discrete recording moments of conventional methods.

FIG. 3 schematically shows ECG 12 representing the movement sequence of the heart (the heart beat of a patient) and comprising movement maxima 14 in uniform spacings, while experience has it that times of lower movement may be found between these movement maxima, i.e. during the slackening of the heart.

In the lower portion of FIG. 3, one recognizes the recording moments 13, which are disposed in correspondence with movement maxima 14 of the heart so that the movement states of the organs moved by the heart beat may be represented in a strobo-scope-like manner via this recording method, respectively before the beginning of systolic cycle 10. Temporal shifting of the recording moments via a time offset is usually possible.

Figure 4:
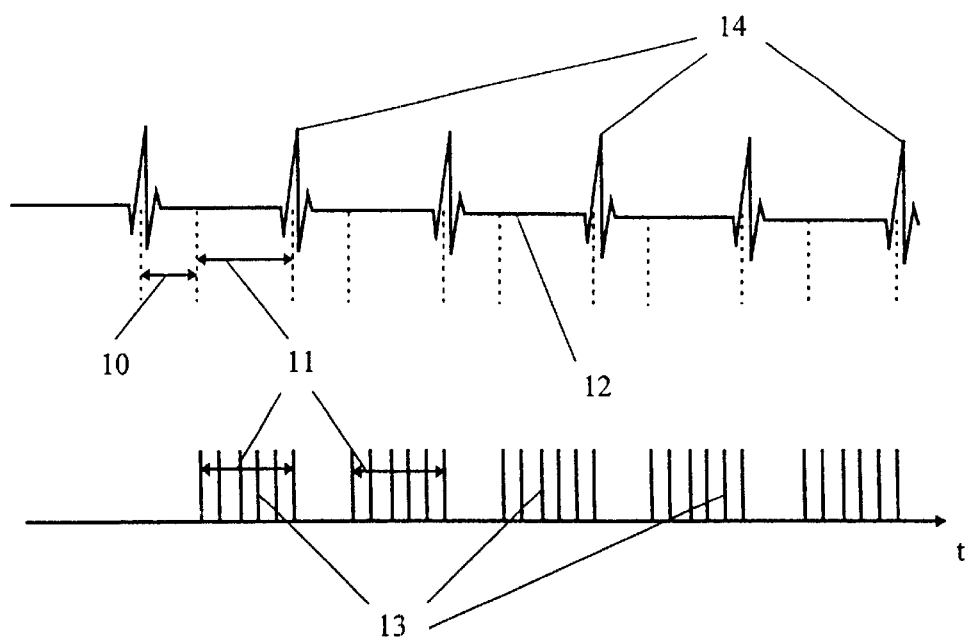
FIG. 4 shows the schematic representation of the heart beat (e.g. ECG) according to FIG. 3 as well as the recording moments during the diastole according to the invention.

FIG. 4 also schematically shows the ECG 12 of a patient, with movement maxima 14. According to the method of the invention, a number of different recording moments 13 are defined which are recorded during diastolic cycle 11. During systolic cycle 10, i.e. during the greatest movement of the heart, no images are taken in order to avoid any movement blur in the three-dimensional ultrasound image. Using this method, the organ respectively to be examined, which is moved by the patient's heart beat, may be represented during diastolic cycle 11, whereby the movement blur of the ultrasound image may be minimized due to a plurality of images of partial image areas taken during diastolic cycle 11. The image recording time is simultaneously shortened many times over.

Figure 5:
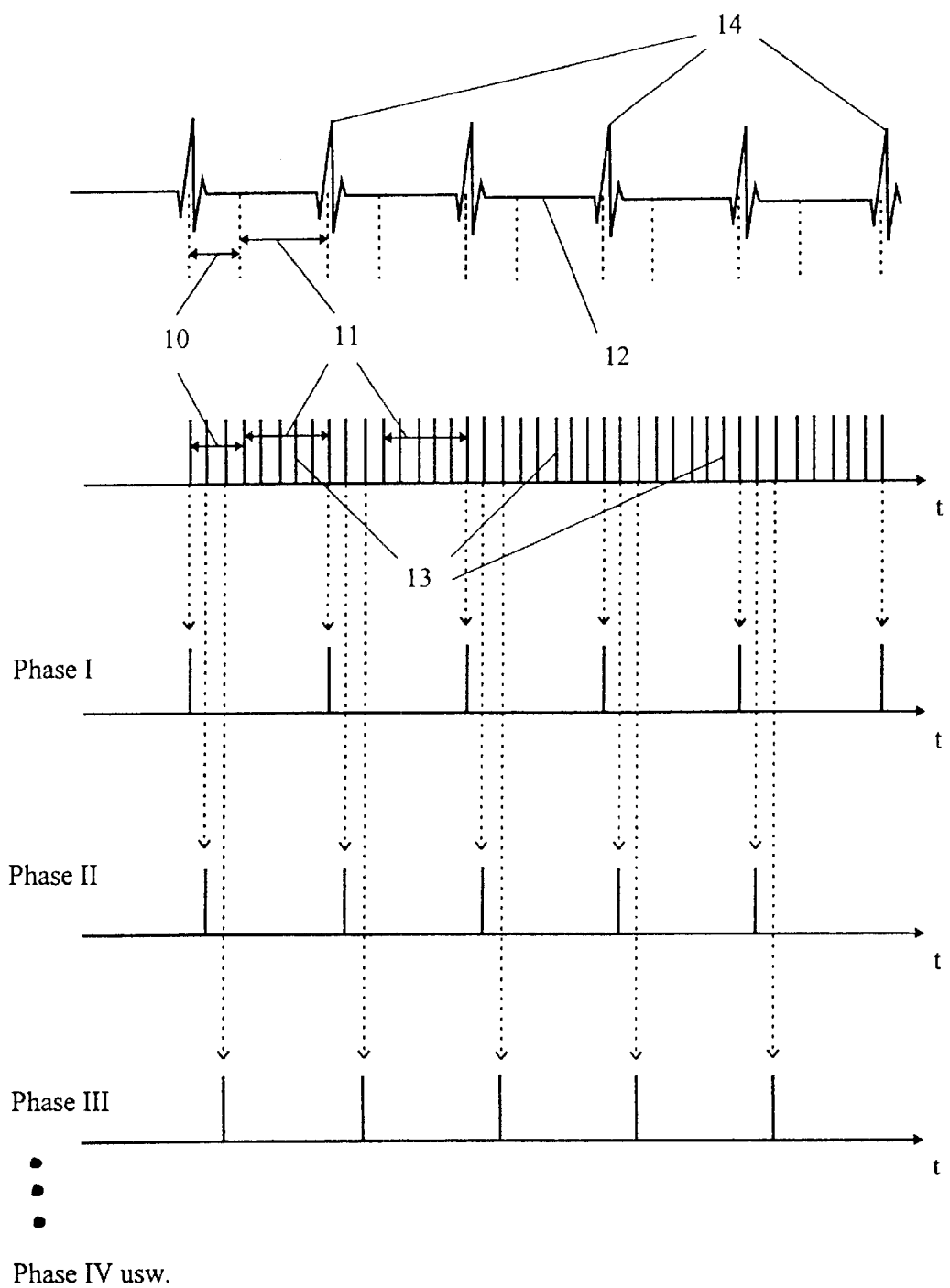
FIG. 5 shows the schematic representation of the heart beat (e.g. ECG) according to FIG. 3 as well as the recording moments of individual movement states and their assignment according to the invention.

FIG. 5 shows the schematic representation of ECG 12 according to FIG. 3 as well as the recording moments of individual movement states and their assignment. Partial image areas 9 are recorded continuously. By assigning individual recording moments, i.e. the corresponding partial image areas 9 to the respective movement states of object 1, there result the corresponding three-dimensional volume images of individual movement states of the object. According to the phase, i.e. according to the movement state of object 1, the individual partial image areas 9 are combined ("piled on top of each other") and result in the representation of a three-dimensional image of object 1 in a specific movement state. By stringing these individual volume images together, there results a real-time representation of the movement of the object like in a film. Thereby, more rapid or slower (slow motion) representations of the movements of the object may also be realized. The data processing system effects selection of the individual recording moments and also carries out the assignment of the individual partial image areas to a volume image.

The foregoing description of the present invention has been presented for purposes of illustration and description. Furthermore, the description is not intended to limit the invention to the form disclosed herein. Consequently, variations and modifications commensurate with the above teachings, in the skilled or knowledge of the relevant art, are within the scope of the present invention. The embodiments described herein above are further intended to disclose best modes for practicing the invention and to enable others skilled in the art to utilize the invention and such, or other, embodiments and with various modifications required by the particular applications or uses of the present invention. It is intended that the appended claims be construed to include alternative embodiments to the extent permitted by the prior art.

What is claimed is:

1. A method for recording ultrasound images of a moving object, comprising:

providing an ultrasound transmitter for emitting ultrasound waves onto the object, and an ultrasound receiver for receiving ultrasound waves reflected from the object, at least one of the ultrasound transmitter and the ultrasound receiver being moved along the object and images of individual partial image areas of the object being taken at specific moments in correspondence with the movements of the object, sensing, in addition to the images of the individual partial image areas, the movement states of the object, assigning the movement states of the object to the images of the individual partial image areas and assembling and representing the images of the individual partial image areas in correspondence with the movement states of the object herein either a plurality of individual partial image areas re recorded continuously for the same movement state of the object and the images of the moments of greatest movement of the object are filtered out by a data processing system, or wherein at the moments of the greatest movement of the object no or only few images are taken and several images are taken of individual partial image areas for the same movement state of the object at moments when the object moves only a little.

2. A method according to claim 1, wherein the moments for recording individual partial image areas of the object are controlled by the movement sequences of the object.

3. A method according to claim 2, wherein the moments for recording individual partial image areas of the object are controlled by signals of the electrocardiogram, the respiration, the gastric peristalsis, the oesophagus peristalsis or a combination of these signals of an organism.

4. A method according to claim 3, wherein for recording blood vessels or organs of an organism, no or only few images are taken during the systolic cycle and several images of individual partial image areas of the blood vessel or the organ are taken during the diastolic cycle.

5. A method according to claim 3, wherein the individual partial image areas of the blood vessel or the organ are recorded at discrete, fixedly defined moments.

6. A method according to claim 3, wherein no images are taken during the systolic cycle and about 2 to 10 images of individual partial image areas of the blood vessel or the organ are taken during the diastolic cycle.

7. A method according to claim 3, wherein the individual partial image areas are combined to form a state image of the object in correspondence with repetitive movement states of the object and represented.

8. A method according to claim 3, wherein the moments for recording individual partial image areas of the object are controlled by means of signals of the electrocardiogram of the living being and individual images of the moments of greatest movement of the object are filtered out by a data processing system.

9. A method according to claim 3, wherein the at least one of the ultrasound transmitter and the ultrasound receiver is moved linearly, circularly, in an arc-shape or in a freehand manner along the object.

10. A method according to claim 3, wherein individual areas of the object, more particularly areas of the object with differing movements, are marked in colors.

11. A method according to claim 2, wherein for recording blood vessels or organs of an organism, no or only few images are taken during the systolic cycle and several images of individual partial image areas of the blood vessel or the organ are taken during the diastolic cycle.

12. A method according to claim 2, wherein the individual partial image areas of the blood vessel or the organ are recorded at discrete, fixedly defined moments.

13. A method according to claim 2, wherein no images are taken during the systolic cycle and about 2 to 10 images of individual partial image areas of the blood vessel or the organ are taken during the diastolic cycle.

14. A method according to claim 2, wherein the individual partial image areas are combined to form a state image of the object in correspondence with repetitive movement states of the object and represented.

15. A method according to claim 2, wherein the moments for recording individual partial image areas of the object are controlled by means of signals of the electrocardiogram of the living being and
individual images of the moments of greatest movement of the object are filtered out by a data processing system.

16. A method according to claim 2, wherein the at least one of the ultrasound transmitter and the ultrasound receiver is moved linearly, circularly, in an arc-shape or in a freehand manner along the object.

17. A method according to claim 2, wherein individual areas of the object, more particularly areas of the object with differing movements, are marked in colors.

18. A method according to claim 1, wherein, for recording blood vessels or organs of an organism, no or only few images are taken during the systolic cycle and several images of individual partial image areas of the blood vessel or the organ are taken during the diastolic cycle.

19. A method according to claim 18, wherein the individual partial image areas of the blood vessel or the organ are recorded at discrete, fixedly defined moments.

20. A method according to claim 18, wherein no images are taken during the systolic cycle and about 2 to 10 images of individual partial image areas of the blood vessel or the organ are taken during the diastolic cycle.

21. A method according to claim 18, wherein the individual partial image areas are combined to form a state image of the object in correspondence with repetitive movement states of the object and represented.

22. A method according to claim 18, wherein the moments for recording individual partial image areas of the object are controlled by means of signals of the electrocardiogram of the living being and
individual images of the moments of greatest movement of the object are filtered out by a data processing system.

23. A method according to claim 18, wherein the at least one of the ultrasound transmitter and the ultrasound receiver is moved linearly, circularly, in an arc-shape or in a freehand manner along the object.

24. A method according to claim 18, wherein individual areas of the object, more particularly areas of the object with differing movements, are marked in colors.

25. A method according to claim 1, wherein the individual partial image areas of the blood vessel or the organ are recorded at discrete, fixedly defined moments.

26. A method according to claim 25, wherein no images are taken during the systolic cycle and about 2 to 10 images of individual partial image areas of the blood vessel or the organ are taken during the diastolic cycle.

27. A method according to claim 25, wherein the individual partial image areas are combined to form a state image of the object in correspondence with repetitive movement states of the object and represented.

28. A method according to claim 25, wherein the moments for recording individual partial image areas of the object are controlled by means of signals of the electrocardiogram of the living being and
individual images of the moments of greatest movement of the object are filtered out by a data processing system.

29. A method according to claim 25, wherein the at least one of the ultrasound transmitter and the ultrasound receiver is moved linearly, circularly, in an arc-shape or in a freehand manner along the object.

30. A method according to claim 25, wherein individual areas of the object, more particularly areas of the object with differing movements, are marked in colors.

31. A method according to claim 1, wherein no images are taken during the systolic cycle and about 2 to 10 images of individual partial image areas of the blood vessel or the organ are taken during the diastolic cycle.

32. A method according to claim 31, wherein the individual partial image areas are combined to form a state image of the object in correspondence with repetitive movement states of the object and represented.

33. A method according to claim 31, wherein the moments for recording individual partial image areas of the object are controlled by means of signals of the electrocardiogram of the living being and
individual images of the moments of greatest movement of the object are filtered out by a data processing system.

34. A method according to claim 31, wherein the at least one of the ultrasound transmitter and the ultrasound receiver is moved linearly, circularly, in an arc-shape or in a freehand manner along the object.

35. A method according to claim 31, wherein individual areas of the object, more particularly areas of the object with differing movements, are marked in colors.

36. A method according to claim 1, wherein the images of individual partial image areas are combined to form a state image of the object in correspondence with repetitive movement states of the object and represented.

37. A method according to claim 36, wherein the moments for recording individual partial image areas of the object are controlled by means of signals of the electrocardiogram of the living being and
individual images of the moments of greatest movement of the object are filtered out by a data processing system.

38. A method according to claim 36, wherein the at least one of the ultrasound transmitter and the ultrasound receiver is moved linearly, circularly, in an arc-shape or in a freehand manner along the object.

39. A method according to claim 36, wherein individual areas of the object, more particularly areas of the object with differing movements, are marked in colors.

40. A method according to claim 36, wherein the state images of individual movement states of the object are represented successively in correspondence with the movement sequence of the object.

41. A method according to claim 40, wherein the at least one of the ultrasound transmitter and the ultrasound receiver is moved linearly, circularly, in an arc-shape or in a freehand manner along the object.

42. A method according to claim 40, wherein individual areas of the object, more particularly areas of the object with differing movements, are marked in colors.

43. A method according to claim 1, wherein the moments for recording individual partial image areas of the object are controlled by means of signals of the electrocardiogram of the living being and individual images of the moments of greatest movement of the object are filtered out by a data processing system.

44. A method according to claim 43, wherein the at least one of the ultrasound transmitter and the ultrasound receiver is moved linearly, circularly, in an arc-shape or in a freehand manner along the object.

45. A method according to claim 43, wherein individual areas of the object, more particularly areas of the object with differing movements, are marked in colors.

46. A method according to claim 1, wherein the at least one of the ultrasound transmitter and the ultrasound receiver is moved linearly, circularly, in an arc-shape or in a freehand manner along the object.

47. A method according to claim 46, wherein individual areas of the object, more particularly areas of the object with differing movements, are marked in colors.

48. A method according to claim 1, wherein individual areas of the object, more particularly areas of the object with differing movements, are marked in colours.

49. A method according to claim 1, wherein the moments for recording individual partial image areas of the object are controlled by means of signals of the electrocardiogram of the living being and that individual images of the moments of greatest movement of the object are filtered out by a data processing system.

50. A method according to claim 1, wherein the ultrasound transmitter and/or the ultrasound receiver is moved linearly, circularly, in an arc-shape or in a freehand manner along the object.

51. A method according to claim 1, wherein individual areas of the object, are marked in colors.

52. An apparatus for obtaining ultrasound images of a moving object, comprising:

an ultrasound transmitter operable to emit ultrasound waves onto the moving object;

an ultrasound receiver operable to receive ultrasound waves reflected from the moving object; and a signal processor connected to said ultrasound transmitter and ultrasound receiver, said signal processor operable to classify movement of the moving object to at least first and second movement states, obtain a plurality of images of the moving object, and to assemble and represent the images of individual partial image areas in correspondence with said movement states of the moving object.

53. An apparatus, as claimed in claim 52, wherein said signal processor is operable to filter out images corresponding to said first movement state and assemble and represent remaining images for the moving object.

54. An apparatus, as claimed in claim 53, wherein said first movement state corresponds to moments of greatest movement in the moving object.

55. An apparatus, as claimed in claim 52, wherein said signal processor is operable to obtain said plurality of images of the moving object only during said second movement state.

56. An apparatus, as claimed in claim 55, wherein said second movement state corresponds to moments of relatively little movement in the moving object.

57. An apparatus, as claimed in claim 52, wherein said signal processor is operable to control recording said images based on the reception of at least one of a signal from an electrocardiogram, a respirator, a gastric peristalsis, and an oesophagus peristalsis.

58. An apparatus, as claimed in claim 52, wherein the moving object is a blood vessel or organ of an organism, and wherein said first movement state corresponds to the systolic cycle of the vessel or organ.

59. An apparatus, as claimed in claim 58, wherein said second movement state corresponds to the diastolic cycle of the blood vessel or organ, and wherein no images are recorded during said first movement state, and about 2 to 10 images of individual partial image areas of the blood vessel or organ are taken during said second movement state.

60. An apparatus, as claimed in claim 52, wherein said images are recorded at discrete, fixedly defined moments.

61. An apparatus, as claimed in claim 52, wherein said images are combined to form a state image of the moving object in correspondence with said movement states.

62. An apparatus, as claimed in claim 61, wherein said state images of individual movement states of the moving object are represented successively in correspondence with the movement sequence of the moving object.

63. An apparatus, as claimed in claim 52, further comprising:

an electrocardiogram operable to receive a signal from a living being and deliver said signal to said signal processor, wherein said signal processor is operable to assign movement of the moving object to at least said first or second movement states based on said signal received from said electrocardiogram.

64. An apparatus, as claimed in claim 52, wherein said signal processor is operable to record individual areas of the moving object, more particularly areas of the moving object with differing movements, in colors.

65. An apparatus for obtaining ultrasound images of a moving object, comprising:

transmitting means for transmitting an ultrasound signal onto the moving object;

receiving means for receiving a reflected ultrasound signal from the moving object and producing a plurality of images of individual partial image areas;

sensing means for sensing movement states of the moving object; and signal processing means coupled to said transmitting means, receiving means, and sensing means, for processing said plurality of images of individual partial image areas and representing a portion of said plurality of images of individual partial image areas based on information from said sensing means.

66. An apparatus, as claimed in claim 65, further comprising:

assigning means connected to said sensing means and signal processing means, for assigning said movement states into one of at least a first movement state and a second movement state, wherein said signal processing means continuously records said plurality of partial image areas filters out images corresponding to said first movement state.

67. An apparatus, as claimed in claim 66, wherein said first movement state corresponds to moments of relatively large movement in the moving object.

68. An apparatus, as claimed in claim 65, further comprising:

assigning means connected to said sensing means and signal processing means, for assigning said movement states into one of at least a first movement state and a second movement state, wherein said signal processing means records only those of said plurality of partial image areas corresponding to said second movement state.

69. An apparatus, as claimed in claim 68, wherein said second movement state corresponds to moments of relatively little movement in the moving object.

70. An apparatus, as claimed in claim 65, wherein the moving object is a blood vessel or organ of an organism, and wherein said first movement state corresponds to the systolic cycle of the vessel or organ.

71. An apparatus, as claimed in claim 70, wherein said second movement state corresponds to the diastolic cycle of the blood vessel or organ, and wherein said image processing means records no images during said first movement state, and about 2 to 10 images of individual partial image areas of the blood vessel or organ during said second movement state.

72. An apparatus, as claimed in claim 65, wherein said images are recorded at discrete, fixedly defined moments.

73. An apparatus, as claimed in claim 65, wherein said images are combined to form a state image of the moving object in correspondence with said movement states.

74. An apparatus, as claimed in claim 73, wherein said state images of individual movement states of the moving object are represented successively in correspondence with the movement sequence of the moving object.

75. An apparatus, as claimed in claim 65, wherein said sending means comprises an electrocardiogram operable to receive an electrocardiogram signal from a living being and deliver said electrocardiogram signal to said assigning means, wherein said assigning means assign movement of the moving object to at least said first or second movement states based on said signal received from said electrocardiogram.

76. An apparatus, as claimed in claim 65, wherein said signal processing means is operable to record individual areas of the moving object, more particularly areas of the moving object with differing movements, in colors.

* * * * *